United States Patent [19]

Gordon

[11] Patent Number: 4,730,253

[45] Date of Patent: Mar. 8, 1988

[54] TESTER FOR MEASURING IMPULSIVITY, VIGILANCE, AND DISTRACTIBILITY

[75] Inventor: Michael Gordon, 301 Ambergate Rd., Dewitt, N.Y. 13214

[73] Assignee: Michael Gordon, Dewitt, N.Y.

[21] Appl. No.: 768,511

[22] Filed: Aug. 22, 1985

Related U.S. Application Data

[63] Continuation-in-part of Ser. No. 508,813, Jun., 1983, abandoned.

[51] Int. Cl.$^4$ .......................... G06F 15/42; G09B 5/00
[52] U.S. Cl. ..................................... 364/415; 434/362
[58] Field of Search ............... 434/201, 258, 307, 308, 434/323, 335, 362; 364/410, 413, 419, 415; 273/1 GE

[56] References Cited

U.S. PATENT DOCUMENTS

| | | | |
|---|---|---|---|
| 3,546,791 | 12/1970 | Koos et al. | 434/323 |
| 3,641,686 | 2/1972 | Krass | 434/258 X |
| 3,675,339 | 7/1972 | LaMarca | 434/231 |
| 3,748,754 | 7/1973 | LaBerge | 434/335 |
| 3,905,132 | 9/1975 | Dyer | 434/323 |
| 3,999,307 | 12/1976 | Tsuda et al. | 434/307 X |
| 4,028,819 | 6/1977 | Walker | 434/258 |
| 4,337,047 | 6/1982 | Hatta | 434/335 X |

OTHER PUBLICATIONS

Metzger, M. A. et al., "Degree of Stereotypic Responding by Hyperactive, Learning Disabled, and Unselected Children in a Computer-Controlled Task", Conference on Human Development-Nashville, Tenn., Apr. 1986.
Anderson, R. et al., "The Assessment and Modification of Hyperkineses: A Review of Programmatic Research at Texas Tech. University", International Scientific Conference of IFLD-Montreal, Canada, Aug. 1976.
Rosvold, H. E. et al., "A Continuous Performance Test of Brain Damage", *Journal of Consulting Psychology*, vol. 20, 1956, 343-352.

*Primary Examiner*—Jerry Smith
*Assistant Examiner*—Clark A. Jablon
*Attorney, Agent, or Firm*—Bruns and Wall

[57] ABSTRACT

A small, portable and inexpensive apparatus, and a testing method using the same, are employed to obtain objective data about children to differentiate between hyperactive and non-hyperactive children. In a Delay Task, the child depresses a button, and after at least a predetermined delay interval depresses the button again. Points are scored if the child waits for a sufficient time, but no point is scored if the child presses the button too soon. In a Vigilance Task, a stream of symbols, which can be numerical digits, is presented in a random or pseudorandom order. If the child sees a "1" followed by a "9", the child is instructed to depress the push-button, but not to otherwise. The number of correct responses, errors of commission, (depressing the button at the wrong time) and errors of omission, (failure to depress the button) are recorded. At the end of the task, the data for the tested child are compared with normative data, and an analysis can be made of the child's tendency toward hyperactivity. A Distractibility Task, similar to the Vigilance Task, uses random flashes of symbols to one or both sides of the relevant symbols. The symbols can be given by synthetic speech, for example for testing blind children or for cross-modal testing. Tracking data, e.g., sequences of symbols before or after errors of commission or omission are recorded, and can be utilized in evaluating the child. An autoboot feature automatically defaults to standard test conditions unless other conditions are selected and entered.

17 Claims, 3 Drawing Figures

TESTER FOR MEASURING IMPULSIVITY, VIGILANCE, AND DISTRACTIBILITY

This application is a continuation-in-part of my co-pending application Ser. No. 508,813, filed June 29, 1983, now abandoned.

BACKGROUND OF THE INVENTION

The present invention is directed to the diagnosis of deficits in attention and behavorial inhibition in children, and is more particularly directed to a system for administering objective tests whereby hyperactivity, attention deficit disorders and learning problems can be assessed objectively.

Hyperactivity among children has been a difficult problem to diagnose accurately, and has been primarily determined based on subjective reports by teachers and parents. The objective measurement of hyperactivity has been attempted in the past, but has not been readily available to teachers or to mental health professionals.

Hyperactivity, or more correctly, Attention Deficit Disorder (ADD) with or without hyperactivity, is a rather common problem among children, and conservative estimates place the incidence of hyperactivity at between 3 and 5 percent of the entire national elementary school population. Hyperactivity is by far the most frequent reason for behavorial consultations with child psychologists, child psychiatrists and pediatricians, and has presented a problem of major proportions in the nation's educational system. Despite the enormity of this problem, there is a large factor of confusion in the understanding surrounding the concept of hyperactivity. One reason for this is the paucity of valid, reliable diagnostic methods currently available. Other reasons are confusion over terminology and a tendency, among health professionals, to view hyperactivity primarily based on his or her own personal value system, theoretical orientation, professional training and general philosophical view of child development.

For many years, mechanical tasks such as the Gardner Steadiness Tester have been used for research purposes. However, these have not found popularity among professionals, largely because of the extreme expense involved in constructing a suitable device. For example, a tester for conducting the Continuous Performance Task would cost over $ 8,000 each to build. Consequently, only a few of these devices exist, and these are located in research organizations, but not at clinics.

Various paper-and-pencil tests have been used in the past to diagnose hyperactivity. These include the Porteus mazes, the Matching Familiar Figures test and some sub-tests of the Wechsler Intelligence Scale for Children-Revised (WISC-R). While some of these tests can discriminate between hyperactive and non-hyperactive groups, the tests are also influenced by other factors, such as visual scanning abilities and intelligence or IQ. Consequently, poor performance on a test such as the Matching Familiar Figures test can indicate either hyperactivity, visual motor deficits, perceptual problems, or some combination of these, but cannot adequately distinguish which is the real problem.

Because of the deficiencies in previously-proposed hyperactivity testing schemes, there is a high risk that a child would be misdiagnosed as hyperactive when a poor test performance was due to other problems. Of course, a misdiagnosed child will not receive the proper treatment, and would not be likely to improve.

Other measures of hyperactivity include questionaires filled out by their parents and/or teachers. As such, these tests rely on the assessments of biased or potentially biased persons, and yield subjective estimates of hyperactivity. These are not always based directly on the child's behavior. However, as clinical practitioners become increasingly conservative in their use of medication, and opt more often for cognitive/behavorial intervention, it becomes more and more important for assessment to be based on a child's actual behavior.

Research in the recent past has pointed to a clear relationship behind hyperactivity in a child and his or her impulsivity. Based on this relationship, the Applicant has previously developed an objective measure of impulsivity based on the child's actual behavior. This is referred to as the "Gordon's Measure of Impulsivity" or "GMI", and is described in the Journal of Abnormal Child Psychology, Vol. 7, No. 3, 1979, pgs. 317-326.

The GMI involves a specialized timing device wherein the subject earned reward points by pressing a response button and waiting a prescribed interval of time before hitting the button again. If the child pressed the response button before the interval response time had elapsed, no points were earned, and the timer was reset. However, if the child waited long enough, a response light went on and a point was scored. At the end of a session, the child was given rewards based on the total reward points earned.

Although the GMI has proven to be useful in objective measurement of impulsivity, further research has shown the latter is only one of several factors that can be used in diagnosing hyperactivity.

Another factor which has been found important in diagnosis is the ability of the child to maintain his attention over a span of time. Still another factor is the distractibility of the child, that is, the tendency for outside events to break the child's concentration. Yet another factor is a comparison of the child's responses across modalities (i.e., between visual and auditory).

OBJECTS AND SUMMARY OF THE INVENTION

It is an object of this invention to provide an easily-administered, game-like system of tasks which measure the levels of impulsivity without interference from other factors such as visual-skills.

It is another object of this invention to produce objective data on a particular child's ability to inhibit behavioral responding.

It is a further object of this invention to provide the capability of testing the child's ability to disregard extraneous, distracting stimuli.

It is yet another object of this invention to provide a testing device, which can easily be constructed as a portable electronic unit, for the administration of separate tasks for measuring the child's capacity to sustain attention, his or her impulsivity, and/or his or her distractibility.

According to an aspect of this invention, method and apparatus are provided for producing precise, valid and efficient diagnosis of attention disorders. According to this invention, at least two measurement tasks are performed: the Delay Task measures the ability to inhibit responding; the Vigilance Task assesses sustained attention and also gives additional data about impulsivity.

The tasks are performed using diagnostic apparatus comprising a housing, a response key on the housing that is manually actuated by the child, a switch for selecting among, e.g., a Delay Task mode and a Vigilance Task mode, symbol generating circuitry for presenting to the child a series of different symbols in which a known symbol is presented for recognition at least several times when the apparatus is in its Vigilance Task mode, delay circuitry for comparing the time between successive actuations of the response key with a predetermined delay time when the apparatus is in the Delay Task mode and producing a reward indication when the subject has waited at least for the length of the programmed delay time after one actuation of the response key before again actuating the same. The child's responses are automatically recorded in a storage device in the apparatus. For the Delay Task, the number of reward indications and the total number of actuations for a predetermined period of time are recorded; for the Vigilance Task, the number of times that the key is depressed when the known symbol is presented under a prescribed condition is recorded as the number of correct responses, the number of times that the key is actuated, other than when the known symbol is presented under that condition, is recorded as the number of errors of commission, and the number of times in the Vigilance Task that the key fails to be actuated when the known symbol is presented under the prescribed condition is recorded as the number of errors of omission.

The Delay Task is administered by setting the apparatus into its Delay Task mode, selecting the delay interval, and suitably instructing the child to depress the response key, then wait for a time and again depress the response key to obtain a "reward". When the task is started, the child begins by depressing the response key, and then alternately waiting and depressing. Each time that the child has waited long enough, a "reward" lamp lights, and the count displayed on the front of the apparatus increases by one. The number of reward events (corresponding to waiting the prescribed amount of time) and the total number of response key actuations are both recorded. After the task is concluded, the number of reward events and the total number of actuations are compared with a standard table of normative data. From this comparison, the child is gauged objectively as being normal, marginal, or abnormal as to impulsivity.

The Vigilance Task is carried out by setting the device into its Vigilance Task mode, suitably instructing the child to depress the response key when a predetermined symbol is presented under certain prescribed conditions, and not to depress the key otherwise. For example, the child is instructed to depress the response key only when he sees a "1" immediately thereafter followed by a "9". This condition is sometimes called a "hot nine".

After the child has been instructed, the apparatus generates a series of different symbols, which can be digits, letters, animal shapes, etc., including several occurrences of the predetermined symbol (i.e. a "1" followed by a "9"), but in a random or pseudorandom order. Then, the apparatus records the number of correct responses, the number of errors of commission, that is, the number of times that the response key was depressed at the wrong time, and the number of errors of omission, that is, the number of times that the child failed to depress the key when he or she should have.

The recorded errors of omission, errors of commission and correct responses are then compared with standard normalized tables, and the child can be objectively classified both in terms of impulsivity and ability to maintain attention over a span of time.

As a further feature of this invention, the apparatus has a Distractibility Task mode, in which random characters flash during a Vigilance Task, but on separate display portions to the left and/or the right of the display where the Vigilance Task characters are displayed. This permits the tester to gather Distractibility Task data about the child, and to obtain other objective information concerning the child's behavior.

The apparatus also keeps tracking data, i.e., it stores the sequences of data immediately before and after errors of commission, in the Vigilance and Distractibility Task modes, and records the interresponse intervals (i.e., time between pushes of the button) in the Delay Task mode. These tracking data provide important clues for the practicioner.

In a preferred version of the apparatus, standard time intervals and block lengths are automatically selected, or "booted-up", but other time intervals and block lengths can be programmed instead by operator intervention.

BRIEF DESCRIPTION OF THE DRAWINGS

The above and many other objects, features and advantages of this invention will be more fully understood from the ensuing detailed description of a preferred embodiment, when considered in connection with the accompanying drawings in which.

DETAILED DESCRIPTION OF A PREFERRED EMBODIMENT

Figure 1:
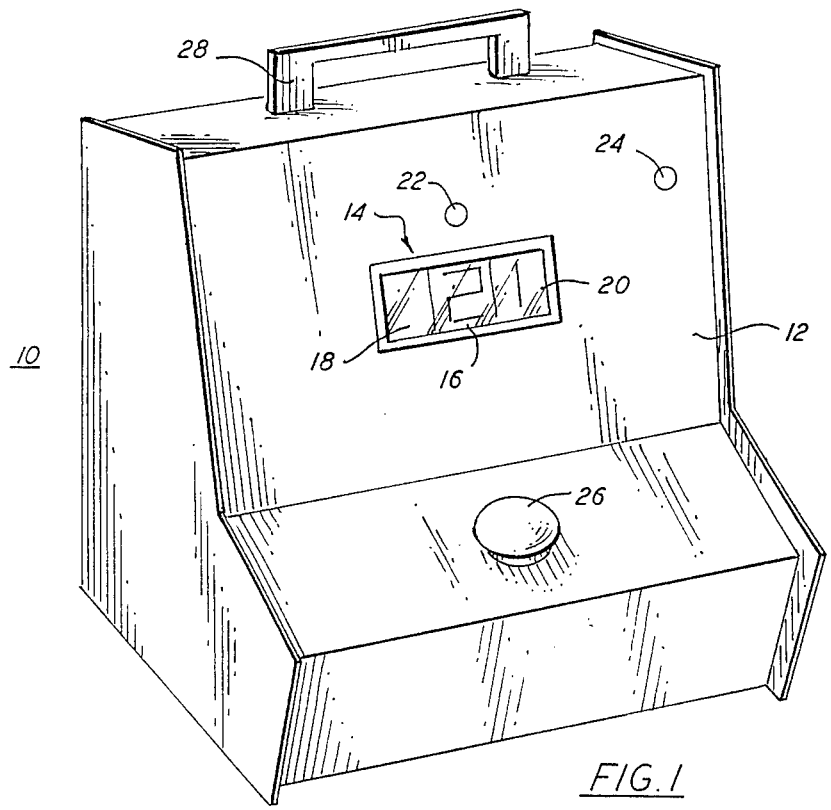
FIG. 1 is a perspective view of the apparatus according to one embodiment of this invention.

With reference to the drawings, and initially to FIG. 1 thereof, testing apparatus 10 according to this invention are here shown as a small, hand portable unit. On a front panel 12 of the apparatus is a three-character alphanumeric display 14 having a central digit 16, left digit 18 and a right digit 20. The display 14 is favorably an LCD, LED or other available, low-power display unit.

A "reward" light 22, a red lamp in this embodiment, is disposed centrally above the display 14, and a green "game over" light 24 is located at the upper right hand part of the front panel 12. A response key or push button 26 is located below the display 14 and a handle 28 is attached to the apparatus 10 at the top. The response button 26 is oversized so that even the youngest child will not have difficulty in locating and pressing it.

Figure 2:
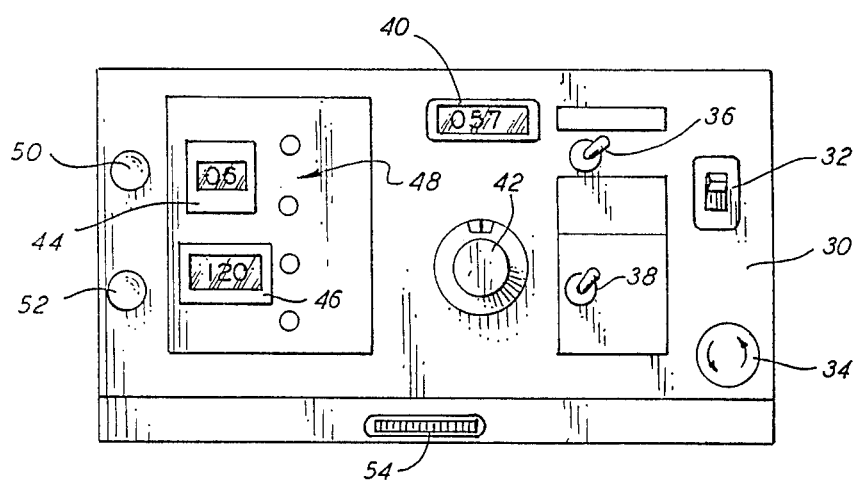
FIG. 2 shows a panel on the back of the apparatus of FIG. 1.

As shown in FIG. 2, a back panel 30 of the apparatus contains various controls to be used by the person administering the test. A power switch 32 and fuse 34 are located at the right-hand side as are a display mode selector switch 36 and an output mode selector switch 38. The display selector switch 36 is favorably a two-position toggle switch to permit selection of the summary stores or tracking data. The output mode selector switch 38 allows the person administering the test to select between sending data directly to a printer or sending it to a computer.

A data display 40 located at the top center of the back panel 30 displays performance data, such as the number of rewards and the number of responses for the Delay Task, or the number of correct responses, errors of commission, or errors of omission of the Vigilance Task or the Distractibility Task. Below this data display 40 is a data/task selector 42 to allow the person administering the tasks to determine which tasks are to be administered or which data are to be displayed.

At the left side of the back panel 30 is a delay interval thumbwheel 44 for setting the delay interval for the Delay Task and the presentation interval for the Vigilance Task and Distractibility Task, and a block length thumbwheel 46 for setting the length of individual time blocks for the various tasks. A set of programmer buttons 48 loads the thumbwheel settings from the thumbwheels 44 and 46 into the system microprocessor memory. The testing apparatus has an autoboot or default feature, in that standard delay intervals, presentation intervals, and block lengths will be automatically selected unless the person administering the tasks enters some other lengths of time on the thumbwheels 44 and 46. Standard parameters are entered for both pre-school and school-aged children.

A reset switch 50 is located at the extreme left side of the back panel 30, and below it is located a start switch 52. The reset switch 50 is depressed for resetting counters and clearing the displays 14 and 40, and the start switch 52 is depressed to begin each individual task.

At the bottom of the back panel 30 is an RS-232 communications connector 54, which enables the electronics of this apparatus to link up with external computer and/or peripherals.

Figure 3:
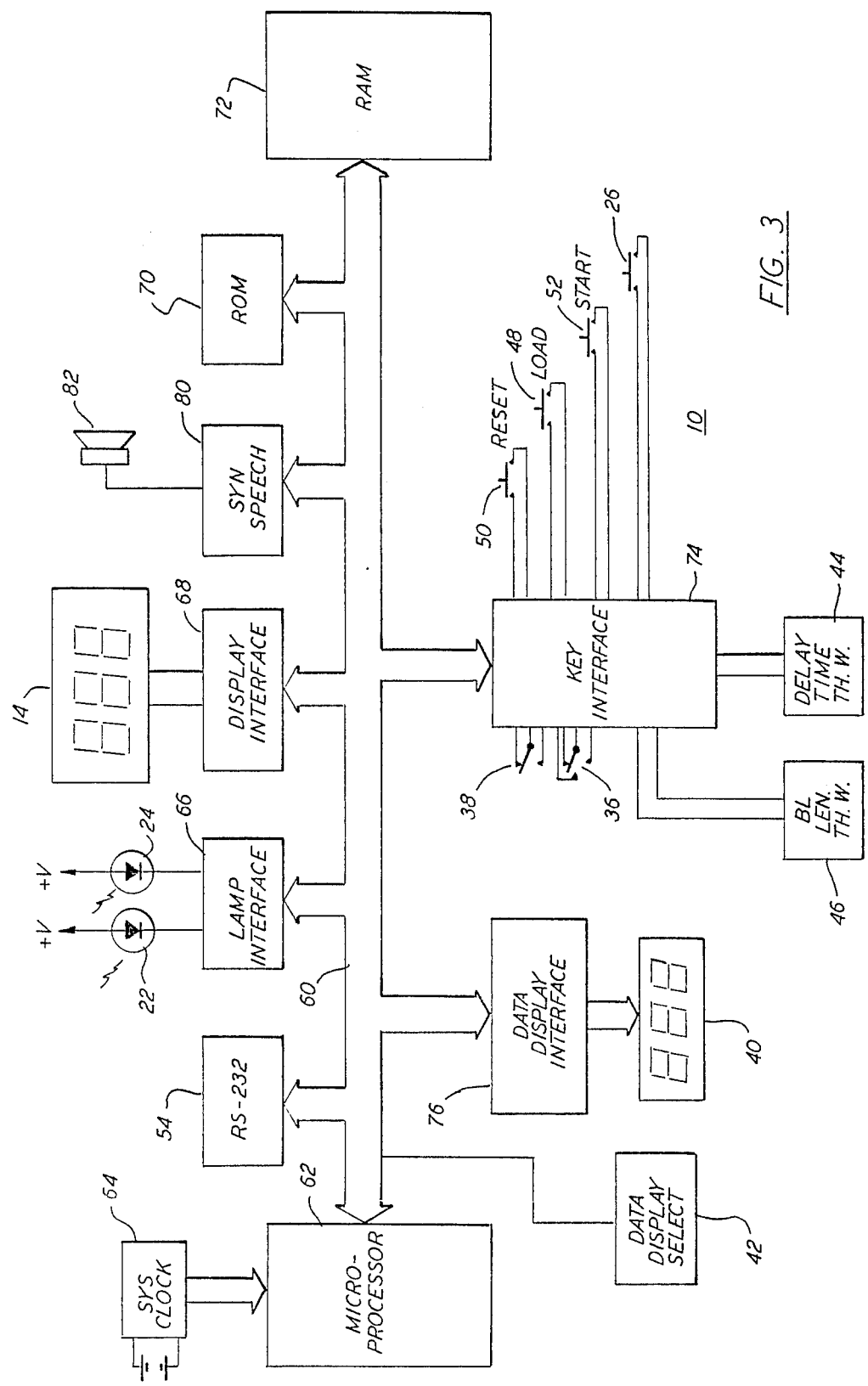
FIG. 3 is a general schematic architectural plan for the electronics of the apparatus of this invention.

The microprocessor system of the apparatus 10 is shown generally in FIG. 3. Here, a clocking signal and data bus 60 is coupled to a microprocessor 62 that is associated with a system clock 64. The microprocessor 62 can, for example, be of any convenient, commercially available type, such as a 6502, 8085, Z-80, 8749, etc. The data bus 60 links the microprocessor 62 to the communications port 54 and to the remaining elements of the system, which are discussed in clockwise order in this drawing. Here, a lamp interface 66 is coupled to the lights 22 and 24, and is operative to light the reward light 22 and the game over light 24, at the appropriate times. Also, a display interface 68, which can favorably be incorporated into the display 14, provides computer-generated digits in random sequence during the Vigilance Task and the Distractibility Task, and provides the number display of reward events during a Delay Task.

A system ROM 70 contains the operating system and utility programs for the various tasks, and a system RAM 72 provides a storage memory for recording the number of responses and the number of reward events during the Delay Task, for storing the number of correct responses, the number of errors of omission and the number of errors of commission, during each block of a Vigilance Task or a Distractability Task. The RAM 72 also can be employed to store the sequence of digits immediately preceding an error of omission or an error of commission.

A key/switch interface 74 is connected to the mode selector switch 38, the task select switch 36, the reset switch 50, the load programmer 48 (here represented as only a single switch), the start switch 52, the response push-button 26, the block-length thumbwheel 46 and the delay-time thumbwheel 44.

A data display interface 76 supplies data to the data display 40, and has an input for receiving control signals from the data selector 42.

Also shown here is an optional synthetic speech generator 80, coupled to an output speaker 82. The synthetic speech generator 80 can be of a well-known circuit design, and thus is not shown in detail here. However, such a circuit 80 would generally include a microprocessor, a synthetic speech ROM, a digital-to-analog converter and an audio amplifier. The synthetic speech generator 80 and the associated speaker 82 can be employed if the tasks are to be administered to children who are blind or who have visual impairments, and can give verbal reinforcement during a Delay Task.

Generally, the rear panel of the apparatus 10 is covered by a cover panel (not shown) and is kept locked down during a task to prevent children from tampering with the controls during operation of the tasks.

When it is desired to test a child, the person administering the tasks plugs in the apparatus 10 and turns on the power switch 32. Unless other times are selected, the apparatus 10 automatically defaults to standard delay intervals, presentation intervals and block lengths.

Generally, the Delay Task is administered before the Vigilance Task, but this is not an absolute requirement.

In the Delay Task, the child is instructed to wait a time (i.e., the delay interval) before pressing the response button 26. If the child has waited long enough, the reward light 22 will shine and the number of rewards, as displayed on the digits 16 and 20 of the display 14, will increment. If the child presses the button 26 before the delay interval has elapsed, then no point is earned, the light 22 stays dark and the delay timer resets.

The apparatus 10 records the Delay Task performance over four successive time blocks. The length of these blocks can be selected from between 1 and 999 seconds, and the delay intervals can be selected between 1 and 99 seconds for each block. The total of responses and the total of reward events for each block is recorded, as are the total for the entire task. Tracking data, i.e., interresponse times for each block, are also stored. The child is not shown when one time block stops and another begins.

Standardization data for the Delay Task were gathered using a six-second delay interval and identical time blocks of 120 seconds each.

After the block sizes and delay intervals are appropriately selected, the four programmer switch push-buttons 48 are depressed, setting the delay interval and block length for the four blocks. The apparatus 10 is now ready to begin the Delay Task.

Suitable instructions, such as the following can be given to the child:

"You're going to play a game in which you will get a chance to win a lot of points. Do you see this light, (pointing to the small red light 22)? Every time you make this light go on you'll earn a point and this counter (pointing to display 14) will keep track of how many points you've won. At the end of the game we'll see how many points you've earned. Now, to make the light go on all you have to do is push this blue button (pointing to the response button 26), and wait a little while before pressing it again. You just press this blue button, wait a while and then press it again. If you press it again too soon, though, you will not get a point, the light won't go on, and you'll have to wait awhile before you can press it to get another point. But if you push the button, wait awhile, then push it again, you'll get a point every time."

At that time, the person administering the tasks can answer any questions and make sure that the child understands the instructions.

When all things are ready, the person administering the task presses the reset switch 50 and then the start switch 52. With the Delay Task under way, the person adminstering the task should sit behind and somewhat to the side of the child so as not to distract him or her. The person administering the tasks can also observe the child's approach to the task and other behavorial elements.

When the task is over, a tone sounds, and the green game over light 24 will light, indicating that the task has been completed.

The Vigilance Task has two modes. In the "1/9" mode, a series of symbols, usually numerals "0" to "9", appear in what appears to be a random fashion on the display 14, and the child is required to press the button 26 every time a "9" appears immediately after a "1". The apparatus 10 records the number of correct presses, the number of times the child failed to press the button 26 upon the appearance of a "1/9" combination (errors of omission), and the number of improper presses of the button 26 (errors of commission). The apparatus also stores tracking data, i.e., sequences of the symbols occurring immedaitely before and after errors of omission and commission. The "1" task is similar but is employed for children under 6 years of age, or for those others who cannot follow the "1/9" instructions. In this mode, the child is told to press the button every time a "1" appears.

In this task, the apparatus 10 records performance on the Vigilance Task over three time blocks. For this task, normative data were derived using three identical time blocks of 180 seconds each, and the standard Vigilance Task uses this block length.

The presentation interval is the time from when a symbol first appears to the appearance of the next symbol. A presentation interval of 1 second was the standard parameter for standardization studies, and is the default or boot-up interval. Numbers appear for two-tenths of a second (i.e., 200 milliseconds), regardless of the presentation interval setting. Thus, if the presentation interval is set at 1 second, the digit or other symbol appears for 0.2 seconds, with a blanking interval of 0.8 seconds. Adjusting the presentation interval only affects the length of the blanking interval.

With the task selector switch 42 set to the standard Vigilance Task mode, the front display 14 is cleared by pressing the reset button 50. The interval and block length are set optionally using the thumbwheels 44 and 46.

The person administering the task gives a suitable instruction to the child, such as the following:

"Now, you're going to play another game. In this game you will see numbers flash on the screen, and I want you to press the blue button (i.e., button 26) only when you see a "9" that comes right after a "1". If the "9" comes after any other number, don't press the button. The only time you should press it is if you see a "9" that comes right after a "1". "Now the red light (i.e., light 22) won't go on at all, but at the end of the game I'll tell you how many points you won. You will know the game is over when the green light (i.e., light 24) goes on. Do you understand?"

Children performing in the "1" mode are told simply to press the button every time the number "1" appears. With very young children it is important first to check that they can recognize the number "1". Of course, if the child has special problems, such as inability to discern one symbol from another, an alternative set of symbols can be employed, such as animal shapes, geometrical figures, objects of various colors, etc.

The Vigilance Task is then started by pressing the reset button 50 and the start button 52. Again, while the child is performing this task, the person administering the task should sit behind the child and to one side. When the task has been completed, a tone sounds and the game-over lamp 24 comes on. The data for the Vigilance Task will be stored as long as the unit is plugged in and turned on and the reset button has not been pressed.

Then, data can be retrieved from the apparatus 10, either by coupling a micro-computer or mini-computer directly to the apparatus by means of the RS-232 port 54, or by viewing the data on the data display 40, using the data selector 42. The data can also be sent directly to a printer.

Data for the Delay Task would include total rewards, total responses, block 1 rewards, block 1 responses, block 2 rewards, block 2 responses, block 3 rewards, block 3 responses, block 4 rewards and block 4 responses. Data for the Vigilance Task would include total correct, block 1 correct, block 1 omissions, block 1 commissions, block 2 correct, block 2 omissions, block 2 commissions, block 3 correct, block 3 omissions and block 3 commissions. Tracking data can include summaries of types of errors, e.g., "1" not followed by a "9" (XIX), and "9" not preceded by "1" (X9X).

The data for each child can be compared with normative data from standardization tables, such as those shown in appendix I. These data are broken down as to age groups and sex of the children. The tables are self-explanatory.

Generally speaking, in the Delay Task, an Efficiency Ratio, which is the ratio of rewards to total responses, can be employed. A child is considered normal, based on comparisons with a statistical group by age. Here the standard data are as in appendix I.

Data from the Vigilance Task can also be employed for diagnosing the child. Children can be classified as normal, borderline, or abnormal, depending on age, by comparing their Vigilance Task performances with the standard data, as for example, in appendix I. Abnormalities from one time block to another can also be detected and used for diagnosis.

The significance of the objective data obtained by these tasks can easily be seen following clinical examples:

In one case, a seven year old girl was referred to the child development clinic by her teacher for poor school performance, not following instructions, missing assignments, and difficulty with reading. The teacher viewed much of this youngster's behavior as willful and oppositional, and was at her wit's end as to how to help the girl learn. Her parents reiterated the teacher's complaints, and added that they felt the child to be distant and aloof much of the time. During the clinical interview this youngster was pleasant and cooperative, but gave the impression of either wanting to be somewhere else or of simply daydreaming.

On the Delay Task she obtained an overall Efficiency Ratio of 0.82, well within the normal range. She earned 46 total rewards. Her responses appeared controlled, orderly, and goal directed. Obviously her difficulties did not lie in the area of impulse control. On the Vigilance Task her difficulties became quite clear. Although she produced just one error of commission, which is well within normal limits, she made 33 errors of omission, scoring well beyond the mean on this measure.

Although her motivation throughout the task was quite good, she was unable to maintain the degree of preparedness required to perform effectively on this part of the task. Therefore, it was possible to identify her main difficulty as a deficit in sustained attention in the absence of impulsivity, which fits the classification of Attention Deficit Disorder with Hyperactivity.

She was placed on a very small dose of stimulant medication, and her teacher was informed of the results of the testing. Intervention strategies were offered for both home and school, and her adjustment improved in a satisfactory manner.

The two GDS tasks used together may also be of considerable help to the clinician in identifying children who are not impulsive or appropriate to classify as ADD.

A ten year old boy was referred to the same clinic for the evaluation of learning problems, difficulties with classmates, much "out-of-seat" behavior, and a variety of other behavior management problems. The parents shared the school's concerns, and were very eager to obtain some pharmaceutical cure for their son.

Three years prior to this evaluation, he had been diagnosed as hyperactive and had been placed on stimulant medication. His parents reported that his initial response to this regimen was good in that he became less active and less of a management problem. They reported that this "honeymoon" period was short-lived, and he quickly became grouchy, irritable, and somewhat depressed. Preferring to have the boy active and boisterous, they terminated his stimulant medication after consulting a pediatrician. However, his problematic behavior persisted, and by the time of this referral, had escalated to the point where some form of intervention was urgently indicated.

This youngster's performance on the Delay Task was solidly in the average range (0.85) with 58 rewards (normal). His responses were orderly and controlled. While he appeared fidgety and restless during his task performance, he did quite well. On the Vigilance Task his scores were also within the normal range, with two errors of omission and only one error of commission. These results firmly suggested that the behaviors which were bringing him into conflict with his environment stemmed from factors other than attentional deficits and impulsivity. Although his behavior truly was impulsive from a descriptive standpoint, he did not demonstrate any deficit in the ability to suppress responding or to sustain attention.

Following the initial evaluation, psychological testing was undertaken to identify the sources of his problem behaviors. It was found that this youngster was frequently overwhelmed by the high goals that he perceived others had set for him. He was terrified of failing in school and felt he could never fulfill his parent's expectations. This gave rise to considerable anxiety, which he discharged motorically through overactivity and impulsive behavior. He was placed in outpatient psychotherapy with a family emphasis, and currently is reported to be doing quite well.

A nine year old boy was referred with complaints of restlessness, noncompliance, fighting with other children, and poor academic performance. While his parents had been recently divorced, these behaviors were longstanding and had been problematic since early childhood. A medical examination by his pediatrician was unremarkable, and he was referred for a psychological evaluation. Upon initial contact with the psychologist, this youngster appeared inhibited, quiet, and withdrawn, giving no indications of impulsive or hyperactive behavior. However, when confronted with the demands of the Dealy Task, the boy was unable to maintain the illusion. He achieved an Efficiency Ratio of 0.44 (less than the 5th percentile) with 28 rewards. His behavior throughout the Delay Task was disjointed, involving much out-of-seat behavior and extreme restlessness. While these behaviors in some ways helped him to suppress responding because he was otherwise occupied, he was nonetheless unable to refrain from emitting a large number of unreinforced responses. This pattern of behavior was repeated during the Vigilance Task. He had a high number of "random errors" and consistently responded immediately after a "1". His performance was clearly suggestive of an inability to delay, particularly once he had been primed to respond. The youngster was placed on a moderate dose of stimulant medication, and was classified as having ADD with Hyperactivity. His academic programming was geared more toward accuracy than speed, and he received resource help to encourage him to modulate his response style. Follow-up contact indicated substantial improvement.

As further enhancements in the Delay Task, the microprocessor 62 and the RAM 72 store the interresponse intervals, i.e. the time between successive presses of the button 26, and the apparatus 10 summarizes these data by generating a listing of the interresponse intervals. For the Vigilance Task, the RAM 72 saves the record of every press of the button 26, and assembles a list of the frequency of digit sequences preceding the button actuations. These data will enable the clinician to make more precise determinations as to the nature of a child's performance and pattern of errors.

For example, when a child makes numerous errors of commission on the Vigilance Task, it is important to the clinician to know where these errors occurred in the sequence of the task. If they occur because the child tries to respond to a "hot nine" combination, but responds too late to be credited with a correct response, this is quite different from the child who responds to the "9" alone when it is not "hot" or who responds to the "1" alone not followed by a "9".

In the Distractibility Task, the same instructions are given as for the Vigilance Task, except the child is also instructed to disregard the numbers presented in the left and right digits 18 and 20 of the front display 14, and to press the button 26 only when a "1" in the central digit 16 is immediately followed by a "9" in the central digit 16. The relevant and extraneous symbols can be presented via synthetic speech, using e.g., left and right earphones or male and female voices. The numbers of correct responses, errors of omission, and errors of commission are collected, as with the Vigilance Task, and the data can be extracted after the task and compared with normative data based on statistical testing of a large number of subjects. Also, as with the Viglance Task, the score data for each block of time within the task are stored, and the stored tracking data can include the sequence of the left and right digit flashes, as well as the sequence of relevant digits.

During the task, however, random or pseudorandom digits appear in the left digit 18 and the right digit 20 of the display 14, and these appear at random or pseudo-random intervals. Relevant digits appear only at the central digit 16. The objective of this task is to measure the degree to which the child is distracted or confused by outside stimuli.

While the apparatus and method of this invention have been discussed with reference to preferred embodiments, it should be understood that the invention is not limited to those precise embodiments, and that many modifications and variations thereof would present themselves to those skilled in the art without departure from the scope and spirit of this invention, as defined in the appended claims.

Appendix I

THRESHOLD TABLES

| ALL AGES Efficiency Ratio Slope | NORMAL 0-±.15 | BORDER-LINE | ABNORMAL <-.15 or >.15 |
|---|---|---|---|
| 3-5 YEAR OLD CHILDREN | NORMAL | BORDER-LINE | ABNORMAL |
| DELAY TASK (N = 150) Efficiency Ratio | | | |
| Total | .61-1.00 | .43-.60 | 0-.42 |
| Block Variab. | .00-0.14 | .15-.25 | ≧.26 |
| Single Block | .61-1.00 | | 0-.40 |
| Responses - Total | 21-66 | 67-89 | ≦20 or ≧90 |
| Correct - Total | ≧26 | 16-25 | 0-15 |
| VIGILANCE TASK (N = 132) Correct | | | |
| Total | 21-29 | 14-20 | 0-13 |
| Single Block | NA | | NA |
| Commissions | | | |
| Total | 0-6 | 7-25 | ≧26 |
| Single Block | 0-1 | | ≧11 |
| Block Variab. | 0-2.07 | 2.08-4.99 | ≧5 |
| 6-7 YEAR OLD CHILDREN | NORMAL | BORDER-LINE | ABNORMAL |
| DELAY TASK (N = 142) Efficiency Ratio | | | |
| Total | .72-1.00 | .42-.71 | 0-.41 |
| Block Variab. | .00-0.11 | .12-.20 | ≧.21 |
| Single Block | .71-1.00 | | 0-.39 |
| Responses - Total | 21-63 | 64-75 | ≦20 or ≧76 |
| Correct - Total | ≧35 | 15-34 | 0-14 |
| VIGILANCE TASK (N = 100) Correct | | | |
| Total | 33-45 | 22-32 | 0-21 |
| Single Block | 12-15 | | 0-6 |
| Commissions | | | |
| Total | 0-10 | 11-23 | ≧24 |
| Single Block | 0-3 | | ≧9 |
| Block Variab. | 0-2.07 | 2.08-4.99 | ≧5 |
| 8-9 YEAR OLD CHILDREN | NORMAL | BORDER-LINE | ABNORMAL |
| DELAY TASK (N = 137) Efficiency Ratio | | | |
| Total | .78-1.00 | .52-.77 | 0-.51 |
| Block Variab. | .00-0.10 | .11-.23 | ≧.24 |
| Single Block | .77-1.00 | | 0-.49 |
| Responses - Total | 21-65 | 66-75 | ≦20 or ≧76 |
| Correct - Total | ≧41 | 22-40 | 0-21 |
| VIGILANCE TASK (N = 96) Correct | | | |
| Total | 40-45 | 33-39 | 0-32 |
| Single Block | 14-15 | | 0-11 |

Appendix I-continued

THRESHOLD TABLES

| ALL AGES Efficiency Ratio Slope | NORMAL 0-±.15 | BORDER-LINE | ABNORMAL <-.15 or >.15 |
|---|---|---|---|
| Commissions | | | |
| Total | 0-8 | 9-21 | ≧22 |
| Single Block | 0-2 | | ≧9 |
| Block Variab. | 0-1.52 | 1.53-3.78 | ≧3.79 |
| 10-11 YEAR OLD CHILDREN | NORMAL | BORDER-LINE | ABNORMAL |
| DELAY TASK (N = 131) Efficiency Ratio | | | |
| Total | .81-1.00 | .55-.80 | 0-.54 |
| Block Variab. | .00-0.11 | .12-.25 | ≧.26 |
| Single Block | .80-1.00 | | 0-.47 |
| Responses - Total | 21-67 | 68-76 | ≦20 or ≧77 |
| Correct - Total | ≧45 | 32-44 | 0-31 |
| VIGILANCE TASK (N = 88) Correct | | | |
| Total | 42-45 | 39-41 | 0-38 |
| Single Block | 14-15 | | 0-12 |
| Commissions | | | |
| Total | 0-3 | 4-15 | ≧16 |
| Single Block | 0-1 | | ≧5 |
| Block Variab. | 0-1.15 | 1.16-1.99 | ≧2 |
| 12-16 YEAR OLD CHILDREN | NORMAL | BORDER-LINE | ABNORMAL |
| DELAY TASK (N = 156) Efficiency Ratio | | | |
| Total | .86-1.00 | .71-.85 | 0-.70 |
| Block Variab. | .00-0.10 | .11-.20 | ≧.21 |
| Single Block | .86-1.00 | | 0-.66 |
| Responses - Total | 21-66 | 67-75 | ≦20 or ≧76 |
| Correct - Total | ≧47 | 39-46 | 0-38 |
| VIGILANCE TASK (N = 156) Correct | | | |
| Total | 43-45 | 40-42 | 0-39 |
| Single Block | 15 | | 0-12 |
| Commissions | | | |
| Total | 0-3 | 4-11 | ≧12 |
| Single Block | 0 | | ≧5 |
| Block Variab. | 0-.99 | 1.00-1.99 | ≧2 |

What is claimed is:

1. A method of diagnosing hyperactivity in a child by measuring the child's attentiveness and impulsivity using a diagnostic device, comprising
    (1) administering a Delay Task including
        (i) setting the device into a Delay Task mode;
        (ii) selecting a delay interval corresponding to a minimum time between successive actuations of a response key on the machine for which to record a reward event for the task;
        (iii) suitably instructing the child to depress the responsive device, wait for a time, and again depress the response key to obtain a reward,
        (iv) starting the child on the Delay Task operation and recording the number of times the key has been actuated and the number of reward events achieved by the child over a prescribed period of time, and
        (v) comparing the number of reward events thus recorded with a standard table of normative data; and
    (b) administering a Vigilance Task including
        (i) setting the device into a Vigilance Task mode,
        (ii) suitably instructing the child to depress said response key when a predetermined symbol is presented, under certain prescribed condition or conditions, on a display, and only to depress the key when the symbol is so presented under said condition or conditions, wherein said prescribed condition or conditions is that the predetermined symbol is followed immediately by a second predetermined symbol such that a correct response is constituted by depressing the response key when the second symbol is presented but only when immediately after presentation of the first-mentioned symbol, (iii) generating a series of different symbols, including several occurrences of said predetermined symbols, in a random or pseudorandom order and presenting said series on said display, (iv) recording as correct responses the number of depressions of said response key when said predetermined symbols are presented under the prescribed condition or conditions, as errors of commission the number of depressions of said key other than when said predetermined symbols are presented under said prescribed condition or conditions, and as errors of omission the number of failures of the child to depress said key when said symbols are presented under said condition or conditions, and (v) comparing the recorded errors of omission, the recorded errors of commission, and the recorded correct responses of said child with standard tables of normative data.

2. The method of claim 1, wherein the prescribed period of time for administering said Delay Task is divided into a plurality of time blocks, and the step of selecting the delay interval includes setting respective different delay intervals for said time blocks.

3. The method of claim 1, wherein the device includes a reward indicator, and the method further comprises turning said reward indicator on when the key is depressed after the child waits at least said minimum time between actuations of the key.

4. The method of claim 1, wherein for each error of commission, a sequence of the series of symbols just preceding the depression of the key is also recorded so that patterns of error can later be detected.

5. The method of claim 1, wherein said series of symbols are visually displayed on a display area on the device.

6. The method of claim 5, further comprising, during said Vigilance Task, generating random symbols to be visually displayed on either side of said series of symbols.

7. The method of claim 1, wherein said series of symbols are audibly generated in a synthetic speech generator.

8. Apparatus for objectively testing a subject's ability to sustain attention and control impulsivity under controlled conditions requiring a positive response comprising a housing, response key means on said housing to be manually actuated by said subject, switch means for switching between a Delay Task mode and a Vigilance Task mode, symbol generating means for presenting to the subject a series of different symbols in which a known symbol is presented for recognition at least several times when the apparatus is in the Vigilance Task mode, delay means for comparing the time between successive actuations of said response key with a predetermined delay time when said apparatus is in the Delay Task mode and producing a reward indication when the subject has waited at least said delay time after one actuation of the response key before again actuating the same, and means for automatically recording the number of reward indications in said Delay Task mode for said subject for a predetermined period of time, as correct responses the number of times in said Vigilance Task mode said key is depressed when said known symbol is presented under a prescribed condition, wherein the prescribed condition of the known symbol is that a set of plural characters including said symbol are presented in a predetermined sequence, as errors of commission the number of times in said Vigilance Task mode said key is actuated other than when said known symbol is presented under said condition, and as errors of omission the number of times in said Vigilance Task mode that said key fails to be actuated when the known symbol is presented under said prescribed condition.

9. The apparatus of claim 8 wherein the symbol generating means includes a display means for visually presenting the symbols to the subject in the form of a stream of alphanumeric characters.

10. The apparatus of claim 8 wherein said symbol generating means further includes programmable means for adjusting the length of presentation periods for said symbols.

11. The apparatus of claim 10 wherein said programmable means includes means for repeating the indicia series during selected blocks of time in which the subject's responses are recorded.

12. The apparatus of claim 8 wherein said means for recording records the number of reward indications for successive separate blocks of time when said apparatus is in the Delay Task mode.

13. The apparatus of claim 8, wherein said means for separately recording records the number of correct responses, errors of commission, and errors of omission for successive separate blocks of time when said apparatus is in the Vigilance Task mode.

14. The apparatus of claim 8, wherein said symbol generating means includes display means on said housing for displaying said symbols as a series of individual alphanumeric characters, and further includes means for generating distraction symbols at random or pseudorandom times to appear on said display means near said alphanumeric characters when the apparatus is in its Vigilance Task mode.

15. The apparatus of claim 8, wherein said means for automatically recording includes storage means for storing, for each recorded error of commission, a sequence of the series of symbols just preceding the actuation of the key so that patterns leading to the errors of commission can be detected.

16. The apparatus of claim 8, wherein said symbol generating means includes a synthetic speech generator for presenting said symbols as audible sounds.

17. The apparatus of claim 8, further comprising interface means for coupling said response key, said generating means, said delay means, and said recording means with micro-computer means for recording the occurrence of each actuation of the response key and summarizing the intervals between key actuations in the Delay Task mode and frequencies of symbol sequences preceding each key actuation in the Vigilance Task mode.

* * * * *